US007823587B2

(12) United States Patent
Müller et al.

(10) Patent No.: US 7,823,587 B2
(45) Date of Patent: Nov. 2, 2010

(54) PROCESS AND SYSTEM FOR MONITORING THE VALVES OF AN ANESTHETIC DISPENSER

(75) Inventors: Jürgen Müller, Lübeck (DE); Rainer Kunz, Lübeck (DE)

(73) Assignee: Dräger Medical AG & Co. KG, Lübeck (DE)

( * ) Notice: Subject to any disclaimer, the term of this patent is extended or adjusted under 35 U.S.C. 154(b) by 1042 days.

(21) Appl. No.: 11/206,879

(22) Filed: Aug. 18, 2005

(65) Prior Publication Data

US 2006/0090758 A1 May 4, 2006

(30) Foreign Application Priority Data

Nov. 3, 2004 (DE) ....................... 10 2004 053 018

(51) Int. Cl.
*A61M 15/00* (2006.01)
*A61M 16/00* (2006.01)
*F16K 31/02* (2006.01)

(52) U.S. Cl. ............................ 128/203.12; 128/203.14; 128/203.25; 128/203.26; 128/203.27; 128/204.21; 128/204.22

(58) Field of Classification Search ............ 128/203.12, 128/203.14, 203.25, 203.26, 203.27, 204.21, 128/204.22
See application file for complete search history.

(56) References Cited

U.S. PATENT DOCUMENTS 4,798,689 A * 1/1989 Heim et al. ................ 261/39.1
5,592,934 A * 1/1997 Thwaites ............... 128/203.12

FOREIGN PATENT DOCUMENTS

EP 0 469 797 B1 2/1992
EP 0469797 B1 * 6/1995

* cited by examiner

*Primary Examiner*—Patricia M Bianco
*Assistant Examiner*—Nihir Patel
(74) *Attorney, Agent, or Firm*—McGlew and Tuttle, P.C.

(57) ABSTRACT

A system and process for monitoring the valves of an anesthetic dispenser with a safety valve (2) and with a dispensing valve (3) for dispensing the anesthetic in the form of a vapor. The valves are connected in series. A system has a downstream dispensing gap (5) and a fixed bypass resistance (9). The dispensing valve (3) is first opened for an equalization time. The safety valve (2) and the dispensing valve (3) are closed and the differential pressure between the saturated vapor branch (4) and the mixed gas branch (8) is measured by means of a differential pressure sensor (6, 7). The safety valve (2) or the dispensing valve (3) is opened and the differential pressure between the saturated vapor branch (4) and the mixed gas branch (8) is measured by means of the differential pressure sensor (6, 7). The opened safety valve (2) or the opened dispensing valve (3) is closed and the difference between the differential pressures measured are determined and compared with a preset limit value, so that the valve (2, 3) that is not opened is considered to be tight when the difference is below this limit value.

22 Claims, 3 Drawing Sheets

1 2,3 4 6,7 5 9 8 28 29 40 24 20 26 20 25 50 21 11 22 23

PROCESS AND SYSTEM FOR MONITORING THE VALVES OF AN ANESTHETIC DISPENSER

CROSS REFERENCE TO RELATED APPLICATIONS

This application claims the benefit of priority under 35 U.S.C. §119 of German Application DE 10 2004 053 018.1 filed Nov. 3, 2004, the entire contents of which are incorporated herein by reference.

FIELD OF THE INVENTION

The present invention pertains to a system and a process for monitoring the valves of an anesthetic dispenser.

BACKGROUND OF THE INVENTION

Such an anesthetic dispenser is disclosed, for example, in EP 0 469 797 B1.

In case of the anesthetic desflurane, which is known per se, the anesthetic tank with the desflurane reservoir to be dispensed is heated in order to achieve a controlled release of the anesthetic in the form of a saturated vapor flow. This occurs due to the low boiling point of desflurane. Mixed gas flowing in from the anesthesia apparatus is sent in the anesthetic dispenser through a fixed resistance, namely, a bypass resistance or bypass gap. The pressure dropping over this fixed resistance is compared with a pressure that drops over a variable settable resistance, namely, a dispensing gap, and through which saturated desflurane vapor flows. By means of the dispensing valve designed as a proportional valve, a controller sets the saturated desflurane vapor flow such that the pressures before the fixed resistance and after the variably settable resistance are equal. As a result, the dispensing of desflurane is set such that the quantity of desflurane being dispensed and consequently the concentration present in the fresh gas released depend only on the position of the handwheel setting the dispensing gap and not on the mixed gas flow flowing in. The controller as well as all safety and test functions are embodied in an electronically programmed manner in this case.

A safety valve (shut-off valve) is located between the heated anesthetic tank and the dispensing valve. Both the dispensing valve and the safety valve must close reliably for the safe use of the anesthetic dispenser described to make sure that in case of a valve defect, the corresponding other valve can reliably interrupt the saturated vapor flow and the patient is thus prevented from being exposed to danger, for example, due to the overdosage of saturated vapor.

If the safety valve had a leak due to a defect, saturated vapor would continue to flow in the direction of the patient in an uncontrolled manner, which could lead to danger for the patient in the extreme case. The object arising from this is to provide a process for monitoring the valves of an anesthetic dispenser with two valves connected in series, which can be carried out safely and in a simple manner.

SUMMARY OF THE INVENTION

It is an object of the invention to provide an improved process for monitoring the valves of an anesthetic dispenser.

According to the invention, a process is provided for monitoring the valves of an anesthetic dispenser with a safety valve connected in series and with a dispensing valve for dispensing the anesthetic in the form a vapor, as well as with a downstream dispensing gap and a fixed bypass resistance. The dispensing valve is first opened for an equalization time. The safety valve and the dispensing valve are closed and the differential pressure between the saturated vapor branch and the mixed gas branch is measured by means of a differential pressure sensor. The safety valve or the dispensing valve is opened and the differential pressure between the saturated vapor branch and the mixed gas branch is measured by means of the differential pressure sensor. The opened safety valve or the opened dispensing valve is closed and the difference between the differential pressures measured with both valves closed and one of the valves open is compared with a preset limit value. The valve not opened in the one of the valves open step is considered to be tight when the difference is below this limit value.

The process may include first opening the dispensing valve in the one of the valves open step. The tightness of the safety valve is measured and evaluated and the safety valve is subsequently opened and the tightness of the dispensing valve is measured and evaluated.

The process may advantageously include precautionary action or an alarm from considering the difference between the differential pressures measured in the both of the valves open step and the one of the valves open step. When the difference does not drop below a preset limit value, all actuators of the anesthetic dispenser are switched to a currentless state and/or an optical and/or acoustic alarm is triggered.

The process may advantageously include using a piezoresistive sensor as the differential pressure sensors. The differential pressure sensor may advantageously be implemented designed as a parallel redundant sensor.

The process may advantageously include using desflurane as the anesthetic.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DESCRIPTION OF THE PREFERRED EMBODIMENTS

Figure 1:
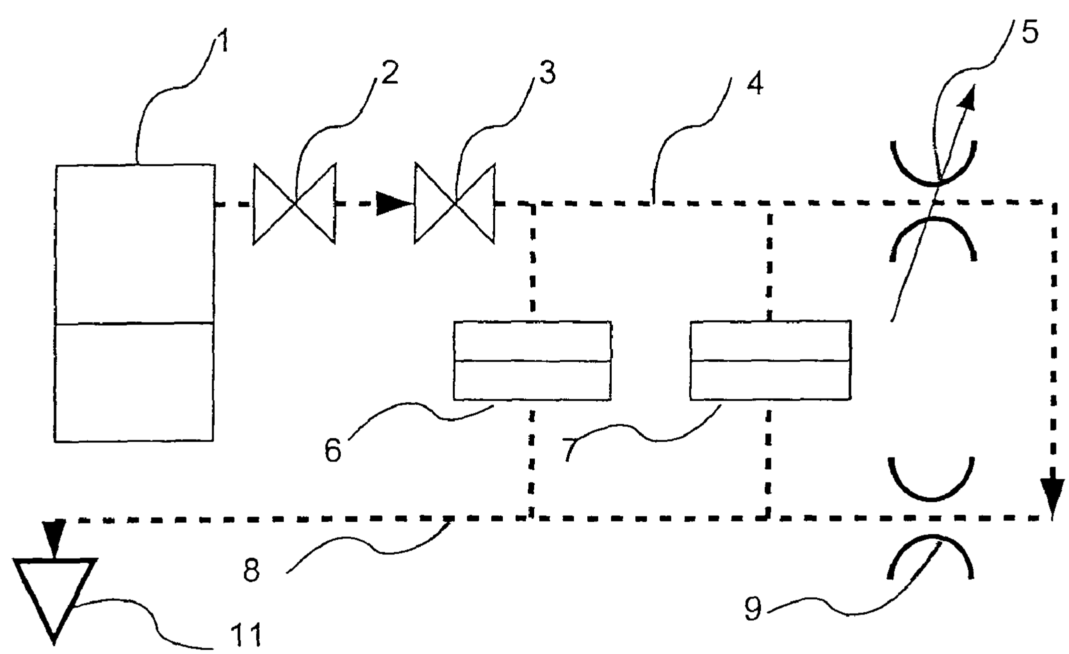
FIG. 1 is a schematic diagram showing a device for carrying out the process for monitoring the valves of an anesthetic dispenser wherein the broken lines represent the saturated anesthetic vapor in the device.

Referring to the drawings in particular, the process uses a system as shown in FIG. 1 with a control that is connected to the actuator of an anesthetic tank 1, a first valve 2 and a second valve 3 as well as two differential pressure sensors 6, 7. Before the anesthetic dispenser begins its dispensing operation or cyclically, when it is in the standby operation, i.e., with the handwheel and consequently with the dispensing gap 5 closed and with the anesthetic tank 1 heated up, the tightness of the first valve 2, which is especially a safety valve, and of the second valve 3, which is especially a dispensing valve, is checked. In case of defect, the anesthetic dispenser is switched into the safe state, i.e., all actuators are now currentless and an optical and/or acoustic alarm is triggered.

The tightness testing takes place in the “handwheel closed” (actuator off) state shown for the correspondingly closed setting of the dispensing gap 5. The different gas flows between the “handwheel closed” state and the “handwheel opened” state which is actuated manually are achieved by means of a pneumatic 5/2-way valve 20 described with reference to FIGS. 2 and 3.

Furthermore, the position of the handwheel is detected by means of electronic switches, which are used as switching recognition means for the pneumatic 5/2-way valve 20. The circuit (of the anesthesia apparatus—with fresh breathing/mixed gas branch) shown is pneumatically connected with the environment via the ventilation opening 11 in the “handwheel closed” position shown (see also FIG. 2). The feed of mixed gas (with anesthetic vapor from the anesthesia tank 1) from the anesthetic apparatus and the feed of fresh gas to the anesthesia apparatus are now switched off. With the handwheel opened and consequently with the dispensing gap 5 opened, mixed gas enters from the anesthesia apparatus breathing gas source (40 in FIGS. 2 and 3), passes through the bypass resistance 9, it is enriched with saturated anesthetic vapor and leaves the anesthetic dispenser via the fresh gas outlet (50 in FIGS. 2 and 3).

Referring to FIG. 1, the following process steps are carried out for checking the tightness of the valves 2, 3, namely, the safety valve or dispensing valve:

1. The second valve 3 is opened at the beginning for an equalization time of, e.g., 20 sec, in order for the pressure to be reduced in the volume between the first valve 2 and the second valve 3 via the dispensing gap 5, the fixed bypass resistance 9 and the ventilation opening 11.

2. Both valves 2 and 3 are closed and an equalization time of, e.g., 2 sec to 3 sec is allowed to pass in order for the pressure in the volume between the second valve 3 and the fixed bypass resistance 9 also to be reduced even if the first valve 2 has a leak. The differential pressure between the saturated vapor branch 4 and the mixed gas branch 8 are then measured by means of the two differential pressure sensors 6, 7.

The valve 2 or 3, which is not being checked now, is opened, and the differential pressure is again measured between the saturated vapor branch 4 and the mixed gas branch 8 after an equalization time of approx. 2 sec.

4. The valve 2 or 3 that is open now is closed and the difference between the differential pressures measured in steps 2 and 3 is determined. If the amount of the difference is below a preset limit, the valve just checked is considered to be tight.

Both valves 2 and 3 are checked for tightness according to the process described during the switch-on test and periodically during standby. Step 1 is to be performed only once per checking the two valves 2, 3. The checking of both valves 2, 3 takes about 30 sec.

The checking may be carried out independently by means of both differential pressure sensors 6, 7 for redundancy. The differential pressure sensors 6, 7 are designed especially as piezoresistive sensors. The redundant, parallel design with two differential pressure sensors 6, 7 is selected for safety reasons, one pressure sensor being sufficient functionally.

The process according to the present invention requires the arrangement of two valves 2, 3 in series, a high pneumatic resistance, a ventilation opening 11, and pneumatic uncoupling from the patient circuit of the anesthesia apparatus. The ventilation and uncoupling are achieved by means of a pneumatic 5/2-way valve 20, which is actuated by the handwheel for setting the dispensing gap 5.

Figure 2:
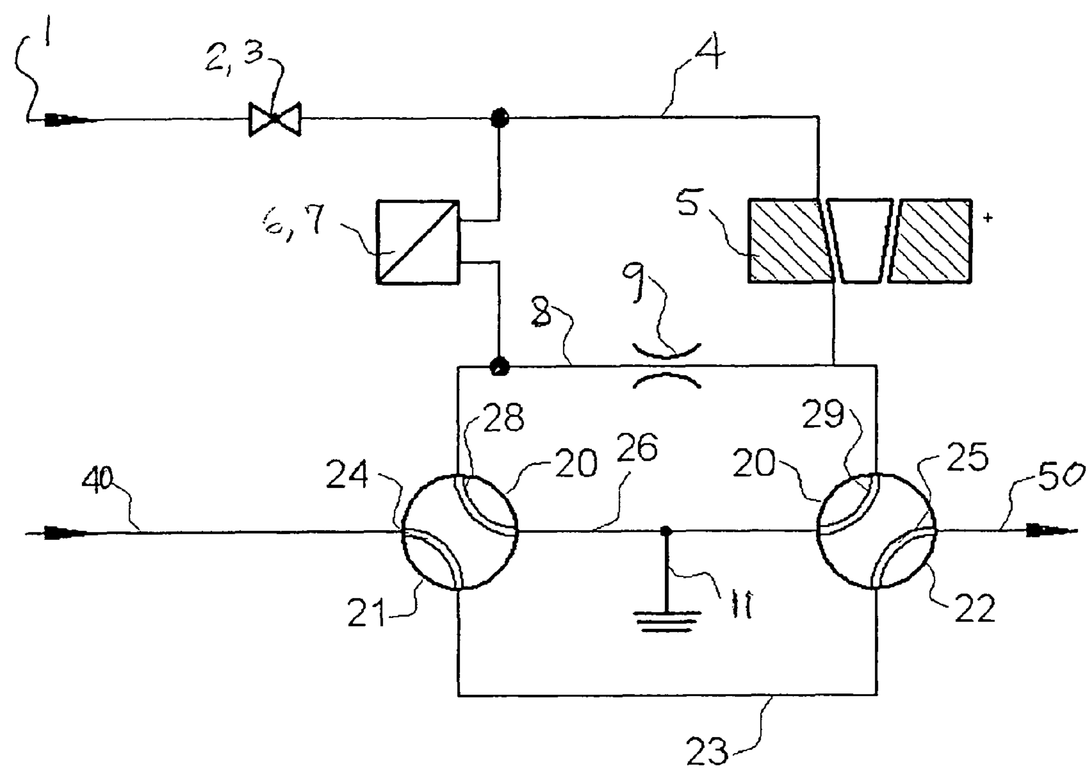
FIG. 2 is a schematic view showing a switchover means according to FIG. 1 in a first switching position.

FIG. 2 shows a valve tightness checking position of the switchover means or 5/2-way valve 20. The 5/2-way valve 20 allows a convenient system whereby the carrier gas flow can be shut off or diverted from the mixed gas branch 8 and the mixed gas branch 8 is connected to the ventilation opening 11. The 5/2-way valve 20 has a first changeover switch 21 and with a second changeover switch 22 shown in a first switch position in FIG. 2. In the first switching position, the carrier gas flows from the gas outlet 40 via a first bypass line 23 to the gas outlet 50. Identical components are designated by the same reference numbers as in FIG. 1. The changeover switches 21, 22 contain gas ducts 24, 25, via which the gas flow from the gas inlet 40 to the gas outlet 50 is made possible via the first bypass line 23. A second bypass line 26 with a ventilation duct 11, which is open toward the environment, is connected with the bypass line or mixed gas branch 8 and with the first throttle 9 via gas ducts 28, 29 of the changeover switches 21, 22 (throttle 9 in FIG. 1 is a simplified showing with this being shown in FIGS. 2 and 3 as part of a flow divider).

In the first switching position of the 5/2-way valve 20, one pneumatic connection of each of the two differential pressure sensors 6, 7 (shown as one unit in FIGS. 1 and 2 to avoid overcrowding) is connected to the ventilation duct 11 via the bypass line or mixed gas branch 8, the gas ducts 28, 29 and the first bypass line 26. The path of the gas in the second pneumatic connection of each of the two differential pressure sensors 6, 7 likewise extends to the ventilation duct 11 via the duct 4, setting the dispensing gap 5, the bypass line or mixed gas branch 8 and the gas ducts 28, 29. Thus, unaffected by the gas flow of the carrier gas, both pneumatic connections of each of the differential pressure sensors 6, 7 are at the atmospheric pressure level with the dispensing gap 5 open.

Figure 3:
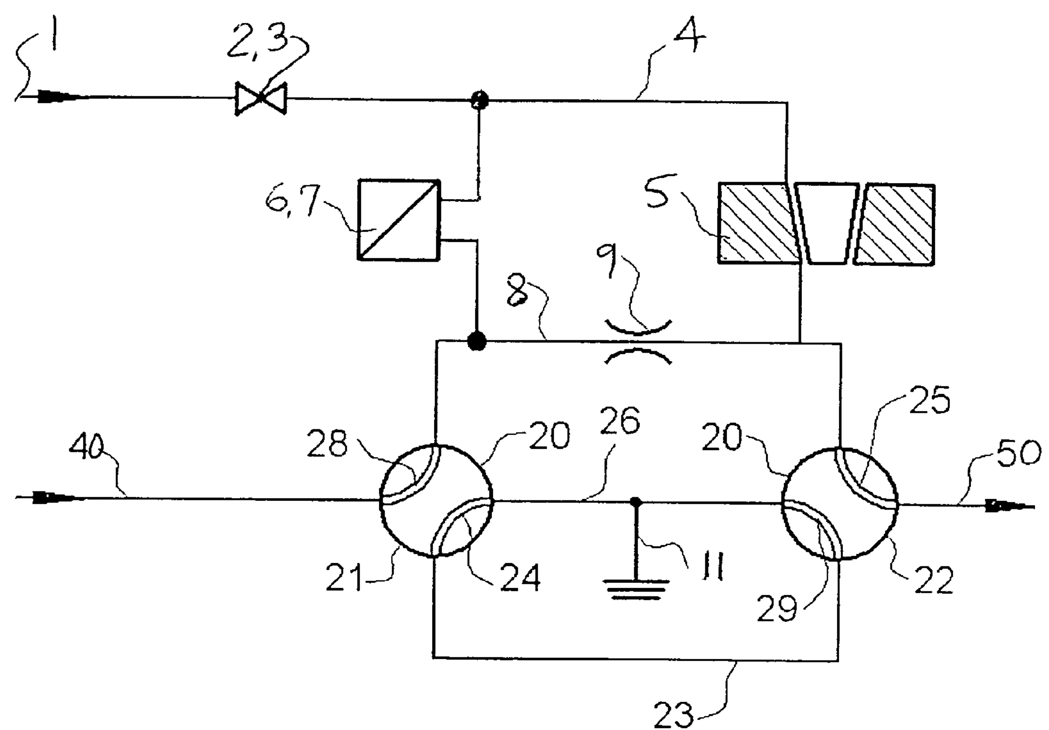
FIG. 3 is a schematic view showing the switchover means according to FIG. 2 in a second switching position.

FIG. 3 shows the second switching position of the 5/2-way valve 20, in which the ventilation duct 11 is connected with the bypass lines 23, 26 via the gas ducts 24, 29 and is thus uncoupled from the bypass line 8. The gas flow of the carrier gas extends over the gas ducts 25, 28 from the gas inlet 40 via the mix gas branch 8 to the gas outlet 50 and can be enriched with anesthetic vapor via the dispensing gap 5.

While specific embodiments of the invention have been shown and described in detail to illustrate the application of the principles of the invention, it will be understood that the invention may be embodied otherwise without departing from such principles.

What is claimed is:

1. A process for monitoring the valves of an anesthetic dispenser with a safety valve connected in series with a dispensing valve for dispensing the anesthetic in the form a vapor, as well as with a saturated vapor branch having a downstream dispensing gap and a mixed gas branch having a fixed bypass resistance, the process comprising the steps of:

(a) providing a mixed gas branch connected to said saturated vapor branch via a dispensing gap;

(b) providing a gas inlet;

(c) providing a gas outlet;

(d) providing a first bypass line and a second bypass line;

(e) providing a ventilation duct which is open toward the environment, said ventilation duct being connected to said second bypass line;

(f) providing a switching means for connecting said gas inlet directly with said gas outlet via said first bypass line and connecting said mixed gas branch and said saturated vapor branch to said ventilation duct via said second bypass line in a gas tightness check position and for connecting said gas inlet to said gas outlet via said mixed gas branch in a non-gas tightness check position;

(g) opening the dispensing valve for an equalization time;

(h) closing the safety valve and the dispensing valve and measuring the differential pressure between the saturated vapor branch and the mixed gas branch by means of a differential pressure sensor;

(i) opening the safety valve or the dispensing valve and measuring the differential pressure between the saturated vapor branch and the mixed gas branch by means of the differential pressure sensor; and (j) closing the opened safety valve or the opened dispensing valve and comparing the difference between the differential pressures measured in steps (h) and (i) with a preset limit value, so that the valve not opened in step (i) is considered to be tight when the difference is below said preset limit value, wherein said steps (g), (h), (i) and (j) are performed when said switching means is in said gas tightness check position.

2. A process in accordance with claim 1, wherein the dispensing valve is first opened in step (i) and the tightness of the safety valve is measured and evaluated and the safety valve is subsequently opened and the tightness of the dispensing valve is measured and evaluated.

3. A process in accordance with claim 2, wherein when the difference between the differential pressures measured in steps (h) and (i) does not drop below a preset limit value, all actuators of the anesthetic dispenser are switched to a currentless state and/or an optical and/or acoustic alarm is triggered.

4. A process in accordance with claim 1, wherein when the difference between the differential pressures measured in steps (h) and (i) does not drop below a preset limit value, all actuators of the anesthetic dispenser are switched to a currentless state and/or an optical and/or acoustic alarm is triggered.

5. A process in accordance with claim 1, wherein a piezoresistive sensor is used as the differential pressure sensor.

6. A process in accordance with claim 5, wherein the differential pressure sensor is a parallel redundant sensor system.

7. A process in accordance with claim 1, wherein the anesthetic used is desflurane.

8. A system in accordance with claim 1, further comprising:

providing a first connection line connected to said differential pressure sensor and connected to said saturated vapor branch at a position upstream of said dispensing gap and downstream of said safety valve and said dispensing valve; and a second connection line connected to said differential pressure sensor and connected to said mixed gas branch at a position upstream of said fixed bypass resistance.

9. A system in accordance with claim 1, wherein said switchover means comprises a first switchover duct and a second switchover duct, said first switchover duct being in communication with said gas inlet, said first bypass line and said gas outlet when said switchover means is in said gas tightness check position such that gas flows from said gas inlet to said gas outlet, said second switchover duct being in communication with said second bypass line, said mixed gas branch and said saturated vapor branch when said switchover means is in said gas tightness check position, said first switchover duct being in communication with said gas inlet, said gas outlet and said mixed gas branch when said switchover means is in said non-gas tightness check position, said second switchover duct being in communication with said first bypass line and said second bypass line when said switchover means is in said non-gas tightness check position.

10. A system in accordance with claim 1, wherein said saturated vapor branch is in communication with said ventilation duct when said switchover means is in said gas tightness check position.

11. A process in accordance with claim 1, wherein said mixed gas branch and said saturated vapor branch are not in communication with said outlet in said gas tightness check position.

12. A valve monitoring system, comprising:

a gas inlet;

a gas outlet;

a ventilation duct which is open toward the environment;

an anesthetic dispenser;

a safety valve connected in series with a dispensing valve for dispensing the anesthetic in the form of a vapor from the anesthetic dispenser, said safety valve being in communication with said anesthetic dispenser;

a saturated vapor branch with a downstream dispensing gap, the saturated vapor branch being connected to the anesthetic dispenser via the series connected valves;

a mixed gas branch having a fixed bypass resistance;

a first bypass line;

a second bypass line connected to said ventilation duct;

a switchover device for switching between a gas tightness check position and a non-gas tightness check position, said switchover device connecting said gas inlet to said gas outlet via said first bypass line and connecting said mixed gas branch and said saturated vapor branch to said second bypass line in said gas tightness check position, said switchover device connecting said gas inlet to said gas outlet via said mixed gas branch in said non-gas tightness check position; and a system valve monitoring procedure control with which the dispensing valve is first opened for an equalization time when said switchover device is in said gas tightness check position, the safety valve and the dispensing valve are closed and the differential pressure between the saturated vapor branch and the mixed gas branch is measured by means of a differential pressure sensor when said switchover device is in said gas tightness check position, the safety valve or the dispensing valve is opened and the differential pressure between the saturated vapor branch and the mixed gas branch is measured by means of the differential pressure sensor when said switchover device is in said gas tightness check position, the opened safety valve or the opened dispensing valve is closed and the difference between the differential pressures measured with both valves closed and one of the valves open is compared with a preset limit value when said switchover device is in said gas tightness check position, the valve not opened in the one of the valves open step is considered to be tight when the difference is below this limit value.

13. A system in accordance with claim 12, wherein the control first opens the dispensing valve for the one of the valves open step and the tightness of the safety valve is measured and evaluated and the safety valve is subsequently opened and the tightness of the dispensing valve is measured and evaluated.

14. A system in accordance with claim 12, wherein the control initiates precautionary action or an alarm from considering the difference between the differential pressures measured in the both of the valves open step and the one of the valves open step when the difference does not drop below a preset limit value.

15. A system in accordance with claim 14, wherein the precautionary action or alarm include switching all actuators of the anesthetic dispenser to a currentless state and/or triggering an optical and/or acoustic alarm is triggered.

16. A system in accordance with claim 15, wherein a piezoresistive sensor is used as the differential pressure sensor.

17. A system in accordance with claim 15, wherein the differential pressure sensor is a parallel redundant sensor system.

18. A system in accordance with claim 12, wherein the anesthetic used in the anesthetic dispenser is desflurane.

19. A system in accordance with claim 12, further comprising:

a first connection line connected to said system valve monitoring procedure control and connected to said saturated vapor branch at a position upstream of said dispensing gap and downstream of said safety valve and said dispensing valve; and a second connection line connected to said system valve monitoring procedure control and connected to said mixed gas branch at a position upstream of said fixed bypass resistance.

20. A system in accordance with claim 12, wherein said saturated vapor branch is in communication with said ventilation duct when said switchover device is in said gas tightness check position.

21. A system in accordance with claim 12, wherein said switchover device comprises a first switchover duct and a second switchover duct, said first switchover duct being in communication with said gas inlet, said first bypass line and said gas outlet when said switchover device is in said gas tightness check position, said second switchover duct being in communication with said second bypass line, said mixed gas branch and said saturated vapor branch when said switchover device is in said gas tightness check position, said first switchover duct being in communication with said gas inlet, said gas outlet and said mixed gas branch when said switchover device is in said non-gas tightness check position, said second switchover duct being in communication with said first bypass line and said second bypass line when said switchover device is in said non-gas tightness check position.

22. A system in accordance with claim 12, wherein said mixed gas branch and said saturated vapor branch are not in communication with said outlet in said gas tightness check position.

* * * * *